United States Patent [19]

Hilverda

[11] Patent Number: Plant 7,144

[45] Date of Patent: Feb. 6, 1990

[54] CARNATION NAMED HILSUCCES

[75] Inventor: Jan J. Hilverda, Aalsmeer, Netherlands

[73] Assignee: Hilverda b.v., Aalsmeer, Netherlands

[21] Appl. No.: 299,771

[22] Filed: Jan. 23, 1989

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new spray carnation cultivar particularly distinguished by its profuse production of relatively small flowers having a light pink coloration borne singly on stems emitted in longitudinally spaced relation from a long, strong and upright main stem having a length of about 60 cm., in average, on a plant having a total height of about 110 cm. and the individual flower stems growing alternately upward on the main stem at such a rate that the flowers appear in a cluster at the top of the main stem.

1 Drawing Sheet

BACKGROUND OF THE NEW PLANT

This spray carnation cultivar originated as a seedling of a hybrid resulting from my crossing two varieties of carnation plants selected from my collection of such plants maintained in my nursery at Aalsmeer, the Netherlands, for breeding purposes, this crossing having been done with the object of providing improvement of the range of varieties available for commercial production of cut flowers. This particular seedling was selected for propagation because of its profuse production of flowers having a very soft pink coloration and propagation of this seedling was done under my direction by means of cuttings at Aalsmeer with such success that I directed that propagation of this variety be carried through several successive generations. This was done at Aalsmeer and demonstrated conclusively that the distinctive characteristics of this new variety would hold true from generation to generation and appeared to be firmly fixed. Propagation of this new plant is presently being carried on at Aalsmeer by means of cuttings.

DESCRIPTION OF THE DRAWING

My new carnation cultivar is illustrated by the accompanying photographic drawing which shows, in full color, the upper portion of a flower stem bearing a plurality of blooms in various stages of maturity, as well as a full face view of a mature bloom, the colors shown being as nearly true as it is reasonably possible to obtain by conventional photographic procedures.

DESCRIPTION OF THE NEW PLANT

The following is a detailed description of my new spray carnation cultivar based upon observations made in the summer of 1988 at Aalsmeer, the color designations being according to the R.H.S. Colour Chart published by The Royal Horticultural Society of London, England.

THE PLANT

Origin: Seedling.

Parentage:

*Seed parent.*—An unnamed and unpatented carnation variety.

*Pollen parent.*—An unnamed and unpatented carnation variety. Both parents were selected by me from among carnation plants in my collection of such plants maintained at Aalsmeer, The Netherlands, for breeding purposes.

Classification:

*Botanic.*—*Dianthus caryophyllus* L.

*Commercial.*—Spray Carnation.

Form: A tall bush having a plurality of stems emitted near the ground.

Height: About 110 cm., in average.

Growth: Rapid, vigorous and upright.

Branching character: Normal.

Foliage:

*Quantity.*—Abundant.

*Size of leaf.*—About 10 to 12 cm. long.

*Shape.*—Elliptic with entire margins.

*Texture.*—Leathery.

*Color.*—Upper side, blue green. Under side, blue green.

*Ribs and veins.*—Prominent midrib.

THE BUD

Size: Medium.

*Diameter.*—About 12 mm.

*Length.*—About 2 to 3 cm.

Form: Cylindrical.

Rate of opening: With mature bud, the flower petals appear in approximately five days.

Color of petals: When sepals first divide, light pink. When petals begin to unfurl, light pink.

Sepals:

*Number.*—5 or 6.

*Shape.*—Generally ovate with an acute apex.

*Character.*—The sepals are hooded over the bud before dividing and stand up as the flower petals unfurl.

*Color.*—Inside, light green. Outside, dark green.

*Striae.*—Only a few being of Light Green/Yellow stripes.

Calyx:

*Size.*—Medium.

*Shape.*—Funnel-shaped.

*Splitting.*—The calyx does not split.

*Aspect.*—Smooth.

Flower stem:

*Length.*—About 60 cm.

*Character.*—Rigid and erect.

*Color.*—Dark green.

THE FLOWER

Blooming habit: Continuous and profusely.
Size of bloom: Small.
*Diameter.*—About 55 mm.
*Depth.*—About 25 mm.
Borne: Singly on stems emitted alternately in longitudinally-spaced relation, there being more than three flowers on each main stem.
Form: When bloom first opens, high-centered When bloom matures, it tends to flatten.
Petalage:
*Number of petals.*—35 to 37, on average.
*Arrangement.*—Imbricated.
*Form.*—Fan-shaped with dentated margin and acute apex.
*Texture.*—Soft.
*Appearance.*—Velvety.
*Color.*—The inside surface of the petals is a Light Pink, approximately R.H.S. 36-D.
Flower stem:
*character.*—Sturdy and upright.
Discoloration after full bloom: None.
Persistence: The flowers hang on and dry.
Disease resistance: Resistant to *Fusarium oxysporum* as observed in growing practice in The Netherlands.
Fragrance: Weak.
Lasting quality: As a cut flower, ten to fourteen days.

REPRODUCTIVE ORGANS

Stamens:

*Number.*—12 to 16.
*Arrangement.*—Uniformly arranged around the ovary.
*Anthers.*—Size: Normal. Color: Cream white.
*Filaments.*—Length: About 10 to 12 cm. long. Color: White.
*Pollen.*—Color: White.
Pistils:
*Number.*—One.
*Styles.*—Length: About 10 to 15 mm. Color: White.
*Stigmas.*—Color: White.

THE FRUIT

Fertility: The fruit is fertile.
Shape: Lozenge-shaped.
Color at maturity: Yellow/Brown.

The variety most nearly resembles 'Lilli-Ann' (unpatented). Compared to 'Lilli-Ann', however, my new variety is distinguished by being a lighter pink in color, has more flower buds per stem, higher production per plant, and a taller growth habit.

I claim:

1. The new and distinct spray carnation cultivar, substantially as herein shown and described, characterized by its profuse production of relatively small flowers having a soft light pink coloration, borne singly on stems emitted in longitudinally-spaced relation on a long, flowering stem having an abundant production of foliage.

* * * * *

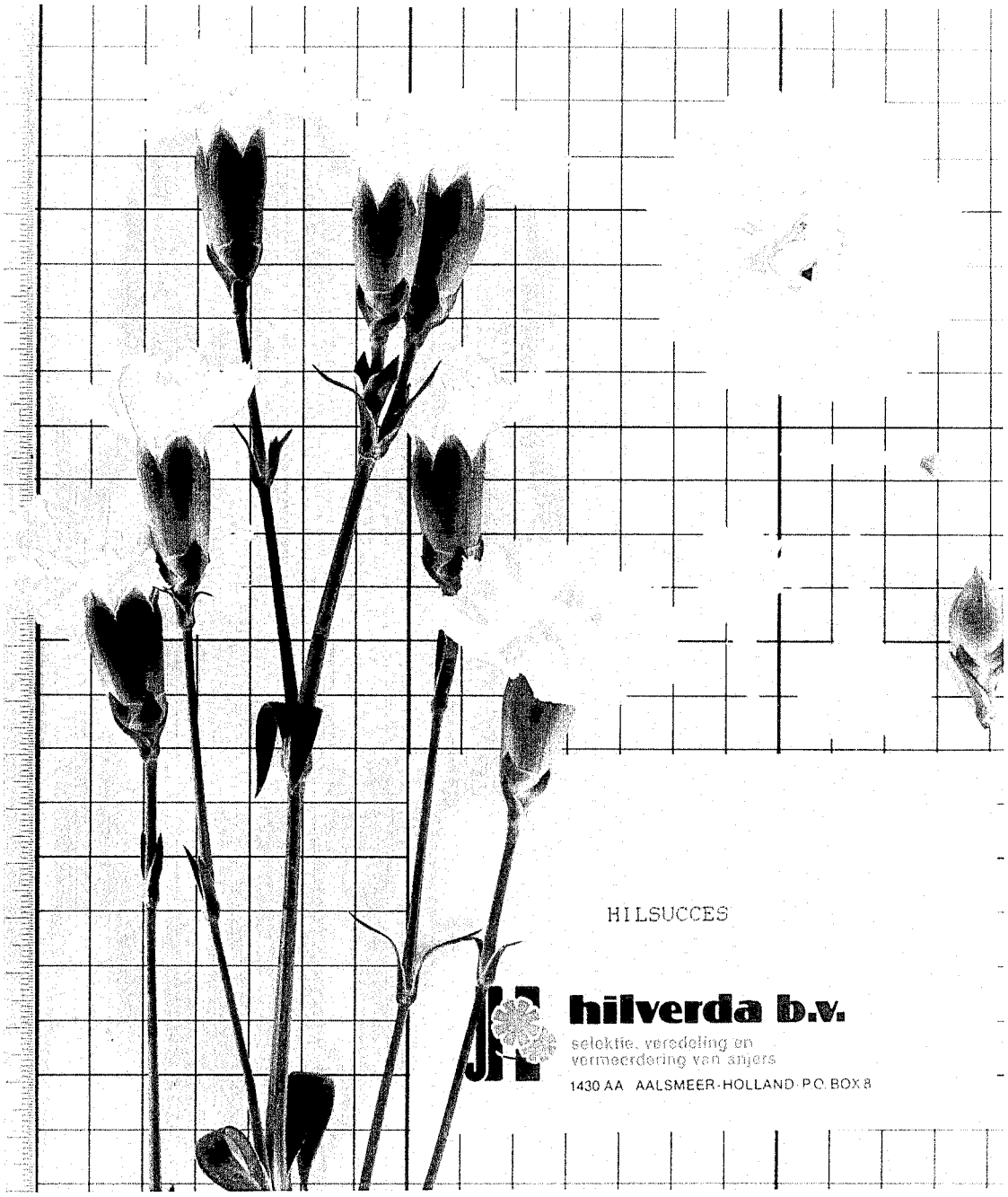
HILSUCCES
hilverda b.v.
selektie, veredeling en
vermeerdering van anjers
1430 AA AALSMEER-HOLLAND P.O. BOX 8